United States Patent
Matsukuma

(10) Patent No.: US 9,409,291 B2
(45) Date of Patent: Aug. 9, 2016

(54) ROBOT SYSTEM, METHOD FOR INSPECTION, AND METHOD FOR PRODUCING INSPECTION OBJECT

(71) Applicant: KABUSHIKI KAISHA YASKAWA DENKI, Kitakyushu (JP)

(72) Inventor: Kenji Matsukuma, Fukuoka (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 0 days.

(21) Appl. No.: 14/526,530

(22) Filed: Oct. 29, 2014

(65) Prior Publication Data
US 2015/0127157 A1    May 7, 2015

(30) Foreign Application Priority Data
Nov. 1, 2013   (JP) .................................. 2013-228585

(51) Int. Cl.
| | | |
|---|---|---|
| *B25J 9/00* | (2006.01) | |
| *B25J 9/16* | (2006.01) | |
| *G01N 35/00* | (2006.01) | |
| *G01N 35/10* | (2006.01) | |
| *G01F 23/292* | (2006.01) | |

(52) U.S. Cl.
CPC .............. *B25J 9/0087* (2013.01); *B25J 9/1682* (2013.01); *B25J 9/1694* (2013.01); *G01F 23/2921* (2013.01); *G01N 35/0099* (2013.01); *G01N 35/1009* (2013.01); *G01N 2035/1025* (2013.01); *G05B 2219/39109* (2013.01); *Y10S 901/09* (2013.01); *Y10S 901/44* (2013.01); *Y10S 901/46* (2013.01)

(58) Field of Classification Search
CPC ...... B25J 9/0087; B25J 9/1682; B25J 9/1694; G01F 23/2921; G01N 35/0099; G01N 35/1009
See application file for complete search history.

(56) References Cited

U.S. PATENT DOCUMENTS

| | | | | |
|---|---|---|---|---|
| 4,415,011 A | * | 11/1983 | Grant ........................ | B65B 3/30 141/284 |
| 4,927,545 A | | 5/1990 | Roginski | |
| 5,265,482 A | * | 11/1993 | Davis .................... | G01F 23/263 73/863.01 |
| 5,338,358 A | * | 8/1994 | Mizusawa .............. | G01N 1/312 118/401 |
| 5,443,791 A | * | 8/1995 | Cathcart ............ | G01N 35/0098 422/561 |
| 6,158,269 A | * | 12/2000 | Dorenkott ............. | G01F 11/021 422/562 |
| 6,562,568 B1 | | 5/2003 | Kleiber et al. | |

(Continued)

FOREIGN PATENT DOCUMENTS

| | | |
|---|---|---|
| JP | 63-289451 | 11/1988 |
| JP | 2004-037320 | 2/2004 |

(Continued)

OTHER PUBLICATIONS

Chinese Office Action for corresponding CN Application No. 201410594296.4, Oct. 29, 2015.

(Continued)

*Primary Examiner* — Nicholas Kiswanto
(74) *Attorney, Agent, or Firm* — Mori & Ward, LLP

(57) ABSTRACT

A robot system according to an embodiment includes a sensor, an arm, and an instructor. The sensor is configured to detect an interface of a liquid. The arm includes a holding mechanism that holds a container containing the liquid. The instructor instructs the arm to cause the container to enter a sensing region of the sensor while holding the container, so as to cause the sensor to detect the interface.

11 Claims, 13 Drawing Sheets

(56) References Cited

U.S. PATENT DOCUMENTS

| | | | |
|---|---|---|---|
| 7,476,290 B2 * | 1/2009 | Saito | B08B 3/02 134/56 R |
| 8,475,740 B2 * | 7/2013 | Watanabe | G01N 35/1009 422/400 |
| 8,715,574 B2 * | 5/2014 | Fritchie | G01N 35/1009 422/509 |
| 2011/0318845 A1 * | 12/2011 | Kurono | G01N 35/0092 436/174 |
| 2014/0106386 A1 | 4/2014 | Umeno et al. | |
| 2015/0231672 A1 * | 8/2015 | Haremaki | B08B 3/04 134/172 |
| 2015/0270146 A1 * | 9/2015 | Yoshihara | H01L 21/67028 134/18 |
| 2015/0314246 A1 * | 11/2015 | Lehtonen | B01F 13/0818 700/265 |

FOREIGN PATENT DOCUMENTS

| | | |
|---|---|---|
| JP | 2007-175060 | 7/2007 |
| WO | WO 2013/002268 | 1/2013 |

OTHER PUBLICATIONS

Japanese Office Action for corresponding JP Application No. 2013-228585, Sep. 15, 2015.
Extended European Search Report for corresponding EP Application No. 14190775.8-1807, Apr. 24, 2015.

\* cited by examiner

ROBOT SYSTEM, METHOD FOR INSPECTION, AND METHOD FOR PRODUCING INSPECTION OBJECT

CROSS-REFERENCE TO RELATED APPLICATION

This application is based upon and claims the benefit of priority of the prior Japanese Patent Application No. 2013-228585, filed on Nov. 1, 2013, the entire contents of which are incorporated herein by reference.

FIELD

The disclosed embodiment relates to a robot system, a method for inspection, and a method for producing an inspection object.

BACKGROUND

Japanese Patent Application Laid-open No. 2007-175060 discloses a robot system in which a robot performs predetermined operations (hereinafter, described as a "bench work") such as pouring or agitating of a reagent, separation, suction of supernatant liquid, heating, and cooling that are given to a specimen such as blood or liquor cerebrospinalis, urine, and a fragment of tissue in a biomedical field.

SUMMARY

A robot system according to one aspect of an embodiment includes a sensor, an arm, and an instructor. The sensor is configured to detect an interface of a liquid. The arm includes a holding mechanism that holds a container containing the liquid. The instructor instructs the arm to cause the container to enter a sensing region of the sensor while holding the container, so as to cause the sensor to detect the interface.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF EMBODIMENT

Hereinafter, in reference to attached drawings, the embodiment of a robot system, a method for inspection, and a method for producing an inspection object that are disclosed in the present application are explained in detail. Here, the present invention is not limited to the embodiment described below.

Hereinafter, the explanation is made by taking a robot that performs a bench work in a biomedical field as an example. A "robot hand" that constitutes an end effector of the robot is named a "hand." Furthermore, a robot arm is named an "arm."

Hereinafter, the explanation is made by taking mainly "pipetting" as a representative example of a bench work. Hereinafter, "an interface of a liquid" is intended to include "the surface of the liquid."

Figure 1A:
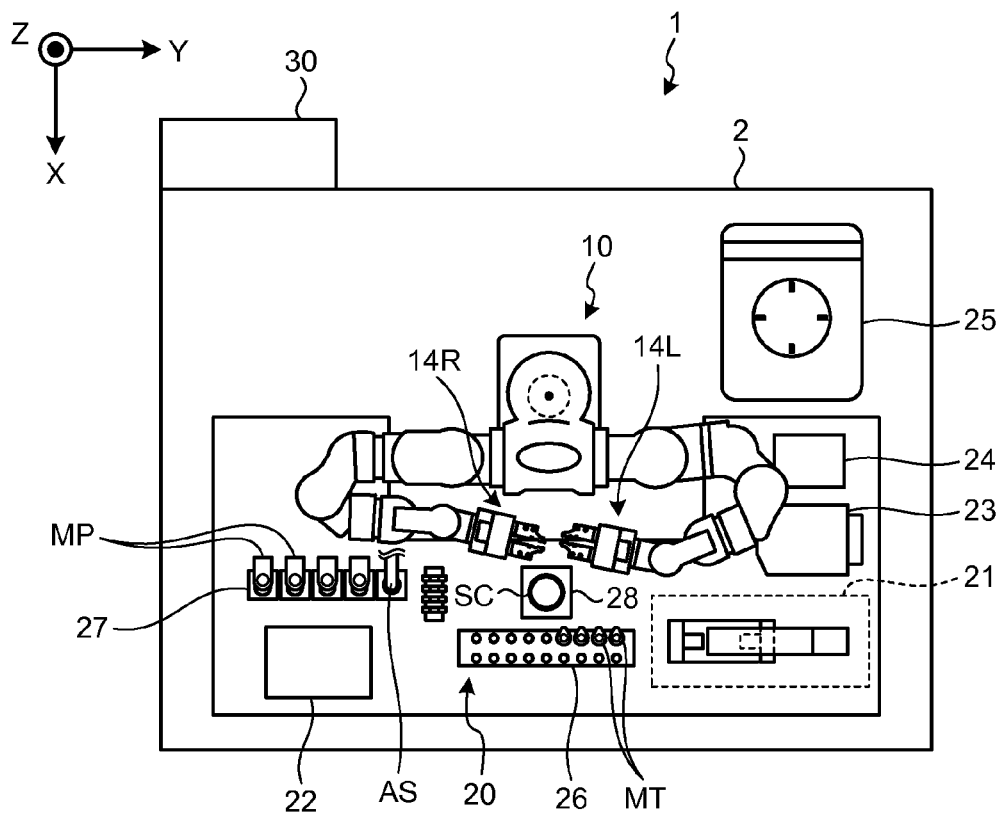
FIG. 1A is a schematic plan view illustrating a constitution of a robot system according to an embodiment.

FIG. 1A is a schematic plan view illustrating a constitution of a robot system 1 according to an embodiment. Furthermore, FIG. 1B is a schematic front view illustrating a constitution of a detection unit 21.

Figure 1B:
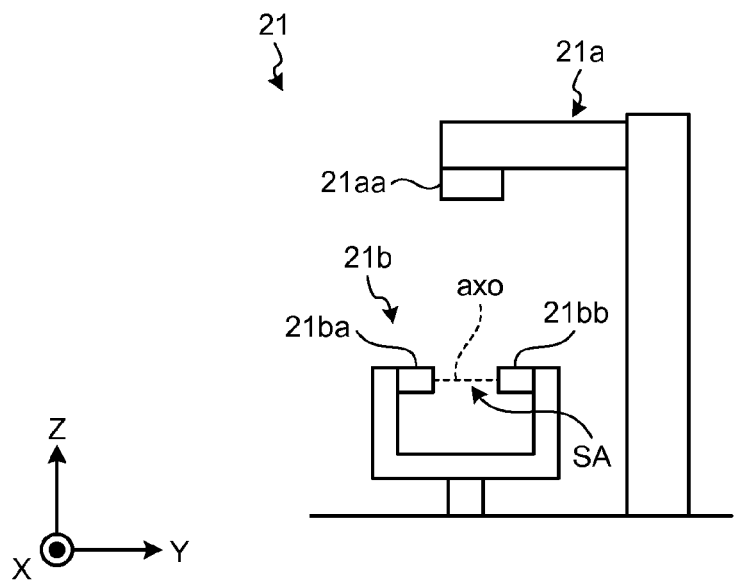
FIG. 1B is a schematic front view illustrating a constitution of a detection unit.

Here, in FIG. 1A and FIG. 1B, for the sake of easily understandable explanations, a three-dimensional orthogonal coordinate system including the Z-axis in which the vertical upward direction on the paper on which each of FIG. 1A and FIG. 1B is drawn corresponds to the positive direction is illustrated. There may be a case that such an orthogonal coordinate system is illustrated also in other drawings used for the following explanations.

As illustrated in FIG. 1A, the robot system 1 includes a safety cabinet 2 having an interior space defined in a rectangular parallelepiped shape. Furthermore, the robot system 1 includes a robot 10, a workbench 20, and various kinds of process apparatuses (described later) in the inside of the safety cabinet 2.

In the present embodiment, the robot 10 is arranged in the inside of the safety cabinet 2. However, depending on work contents, a working-use cabinet corresponding to an application, such as a draft chamber or a clean bench, is applicable in place of the safety cabinet 2. Furthermore, it may be possible to adopt the constitution in which the robot 10 is arranged outside the safety cabinet 2 or the like, and operated in a state that a right hand 14R and a left hand 14L enter inside the safety cabinet 2 through a front door or the like of the safety cabinet 2.

As the process apparatus, for example, as illustrated in FIG. 1A, a detection unit 21, an incubator 22, a heating and cooling unit 23, an agitator 24, a centrifugal machine 25, a test-tube stand 26, a pipette stand 27, a schale stand 28, and the like are listed.

The test-tube stand 26 holds a micro tube MT, the pipette stand 27 holds a suction implement such as a pipette MP or a vacuum type suction implement AS, and the schale stand 28 holds a schale SC. The micro tube MT, the pipette MP, the vacuum type suction implement AS, and the schale SC are also included in the process apparatus.

Furthermore, the robot system 1 includes a controller 30 outside the safety cabinet 2. The controller 30 is connected to the respective apparatuses including the robot 10 that are arranged in the inside of the safety cabinet 2 in a communicable manner. The connection between the controller 30 and the respective apparatuses imposes no restriction on a connection configuration such as a wired connection or a wireless connection.

Here, the controller 30 is a controller that controls the operation of the respective apparatuses connected thereto, and includes various kinds of control devices, an arithmetic processing units, storage units, and the like. The specific constitution of the controller 30 is explained later in conjunction with FIG. 2. The controller 30 may be arranged in the inside of the safety cabinet 2.

The robot 10 is a dual-arm type manipulator that is operated upon receiving operation instructions from the controller 30, and includes the right hand 14R and the left hand 14L that are mounted on a right arm and a left arm thereof, respectively. The robot 10 including the right hand 14R and the left hand 14L is specifically explained later in conjunction with FIG. 3A and subsequent drawings.

The workbench 20 constitutes a work space for the robot 10 to perform each bench work by using the process apparatuses. On the workbench 20, for example, the robot 10 performs the operation of pipetting a liquid contained in the micro tube MT by the pipette MP gripped by using the right hand 14R, while gripping the micro tube MT by using the left hand 14L.

Here, the operation of the robot 10 is based on a "job" that is a specific program for operating the robot 10. The "job" is registered into the controller 30 or the like in advance via an input device (a programming pendant or the like) that is not illustrated in the drawings.

The controller 30 generates operation signals that operate the robot 10 based on the "job", and outputs the signals to the robot 10. The operation signals are generated, for example, as pulse signals transmitted to a servo motor mounted on each of joint parts of the robot 10.

Here, in performing the pipetting or the like, according to the conventional technique, the interface level of a liquid (hereinafter, referred to as a "liquid interface level" in some cases) in the micro tube MT is not detected, and the distal end of the pipette MP is entered down to an approximate position below the interface of the liquid to suck the liquid, in many cases.

Accordingly, when the quantity of a liquid in the micro tube MT is changed by being sucked, or when precipitates are produced, there has been a case in which the sucking of a predetermined quantity of the liquid is failed, or precipitates are mixed in a sucked liquid even when it is necessary to suck only a supernatant liquid. That is, in performing a bench work with high accuracy and high reproducibility, there has been much room for improvement.

Accordingly, in the present embodiment, while detecting the liquid interface level, the robot 10 performs a bench works such as the pipetting. The detection unit 21 constitutes a unit that enables the robot 10 to perform the bench work while detecting the liquid interface level.

As illustrated in FIG. 1B, the detection unit 21 includes a jig 21a and a sensor 21b. The jig 21a has a support column mounted upright on the workbench 20, and a contact part 21aa provided to the support column in a suspended manner from the distal end of the support column. The tail part MP-T (described later) of the pipette MP is thrust against the contact part 21aa. This operation is explained later in conjunction with FIG. 7A and subsequent drawings.

The sensor 21b has a light emitting part 21ba and a light sensing part 21bb, and is an optical sensor in which the region of an optical axis axo formed constitutes a sensing region SA. The sensor 21b functions as a liquid level sensor configured to detect the interface of a liquid by the change of the transmission amount, a refractive index, or the like at the optical axis axo in the sensing region SA. Means for detecting the interface of a liquid in appended claims corresponds to the sensor 21b, and a detection region of the means for detecting corresponds to the sensing region SA.

Here, the sensor 21b is arranged in such a manner that the optical axis axo is substantially parallel to the horizontal direction (a direction along the XY plane in FIG. 1B).

In the present embodiment, in performing pipetting or the like, the operation of the robot 10 is controlled so that the accurate pipetting is performable while the liquid interface level is detected by using the detection unit 21. This operation is specifically explained later in conjunction with FIG. 6A and subsequent drawings.

Figure 2:
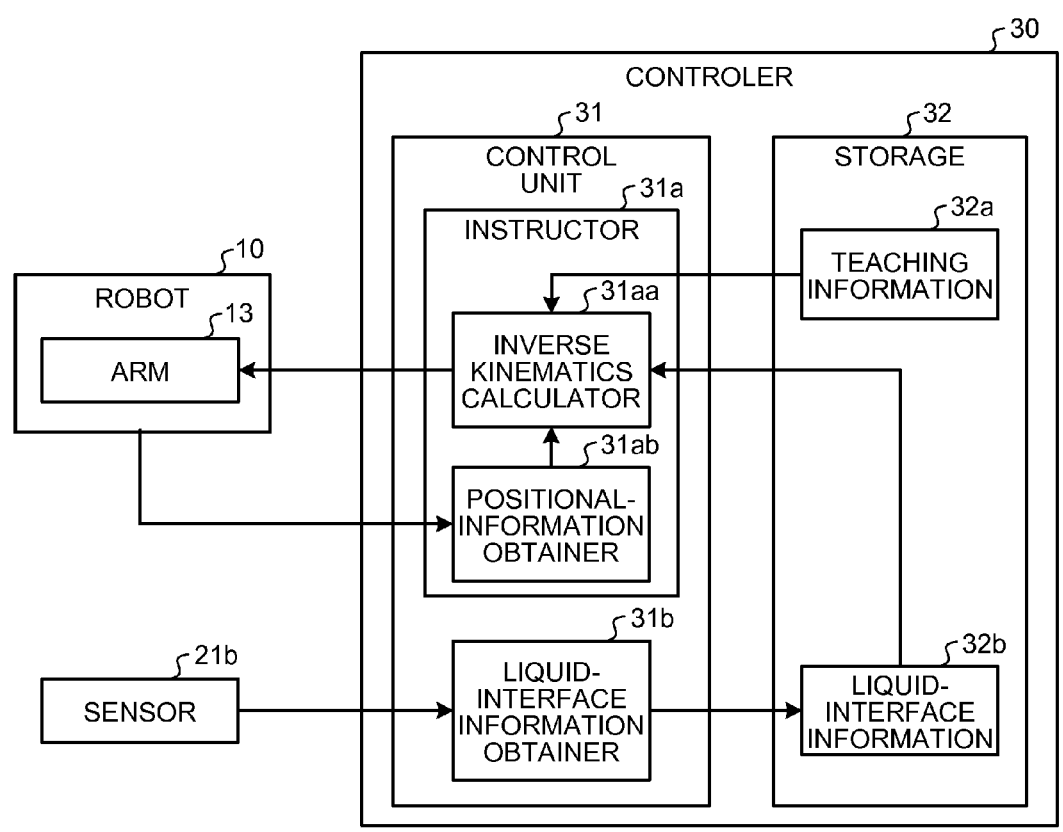
FIG. 2 is a block diagram of the robot system in the embodiment.

Next, the configuration of the robot system 1 according to the embodiment is explained in conjunction with FIG. 2. FIG. 2 is a block diagram of the robot system 1 in the embodiment. In FIG. 2, only constitutional features required for explaining the robot system 1 are illustrated, and the descriptions of general constitutional features are omitted.

Furthermore, in the explanation made in conjunction with FIG. 2, the internal configuration of the controller 30 is mainly explained, and the explanations of the various kinds of devices and the process apparatuses that are already illustrated in FIG. 1A may be simplified or omitted.

As illustrated in FIG. 2, the controller 30 includes a control unit 31 and a storage 32. The control unit 31 further includes an instructor 31a and a liquid-interface information obtainer 31b. Furthermore, the instructor 31a includes an inverse kinematics calculator 31aa and a positional-information obtainer 31ab.

The storage 32 is a storage device such as a hard disk drive or a nonvolatile memory, and stores teaching information 32a and liquid-interface information 32b.

Here, it is unnecessary to arrange all the respective constitutional features of the controller 30 illustrated in FIG. 2 in the controller 30 per se. For example, either one of or both of the teaching information 32a and the liquid-interface information 32b that are to be stored in the storage 32 may be stored in an internal memory provided in the robot 10. Alternatively, an upper device of the controller 30 may store the teaching information 32a and the liquid-interface information 32b so that the controller 30 appropriately obtains the information from the upper device.

The control unit 31 performs the overall control of the controller 30. The instructor 31a generates operation signals that operates the robot 10 including an arm 13 based on the teaching information 32a registered in advance and the liquid-interface information 32b to be appropriately updated by liquid-interface information obtainer 31b, and outputs the signals to the robot 10. In the appended claims, means for holding and transferring a container in which a liquid is contained corresponds to the arm 13. Furthermore, means for instructing the means for holding and transferring to cause the container to enter the detection region of the means for detecting while holding the container so as to cause the means for detecting to detect a liquid interface corresponds to the instructor 31a.

Here, the teaching information 32a includes the "job" that is a specific program for actually operating the robot 10 depending on the type or the like of a bench work. The instructor 31a determines the manner of operation of the robot 10 in consideration of the various kinds of information such as the liquid interface level included in the liquid-interface information 32b as a parameter with respect to the "job."

The inverse kinematics operation is performed in the inverse kinematics calculator 31aa to calculate the operating position of each of joint parts of the arm 13. In addition, based on this operation, the inverse kinematics calculator 31aa provides operation signals that operate each of the servo motors mounted on the respective joint parts of the arm 13 to each servo motor in each operation period.

The operation signals are, for example, generated as pulse signals provided to each of the above-mentioned servo motors. Furthermore, the controller 30 obtains a position signal (pulse signal) that indicates the rotational position thereof from an encoder with which each servo motor is provided, and the positional-information obtainer 31ab obtains the positional information (or the posture information) of the arm 13 depending on the resolution of the encoder. The positional information obtained by the positional-information obtainer 31ab is notified to the inverse kinematics calculator 31aa.

The liquid-interface information obtainer 31b obtains appropriately an ON signal or an OFF signal that is output from the sensor 21b, and derives a liquid interface level from the positional information or the like of the arm 13 at the time of acquiring these signals. The liquid-interface information obtainer 31b stores the liquid-interface information 32b including the derived liquid interface level in the storage 32.

Here, the sensor 21b outputs an ON signal when a liquid is detected, and outputs an OFF signal when the upper surface of the liquid (that is, the interface of the liquid) is detected. This operation is specifically explained later in conjunction with FIG. 6A to FIG. 6D.

Hereinafter, one example of the constitution of the robot 10 that is operated based on instructions of the instructor 31a, and one example of a pipetting operation in the robot system 1 are specifically explained in the order given above.

Figure 3A:
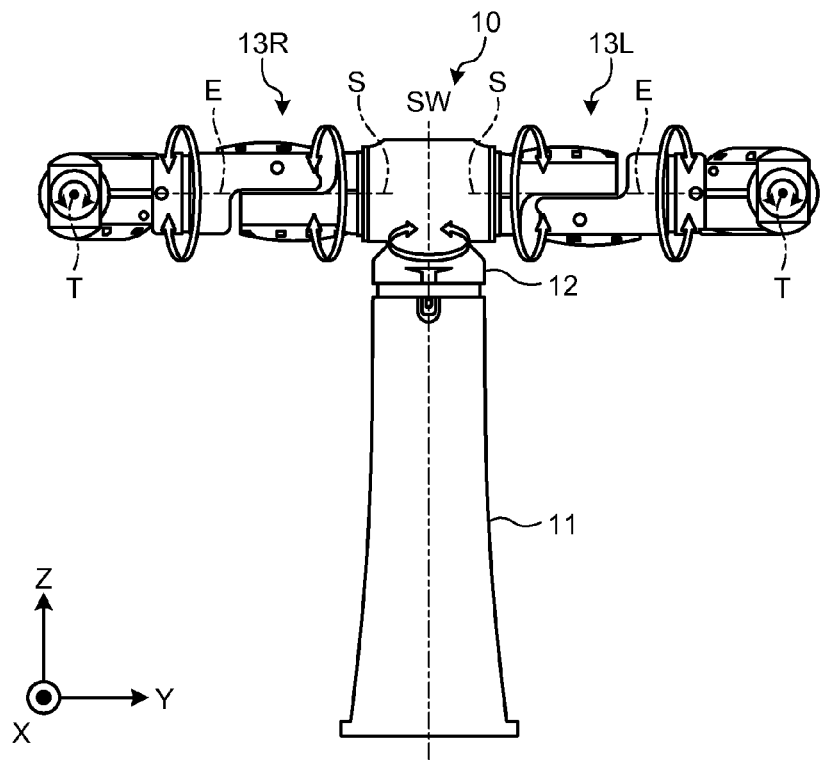
FIG. 3A is a schematic front view illustrating a constitution of a robot.
Figure 3B:
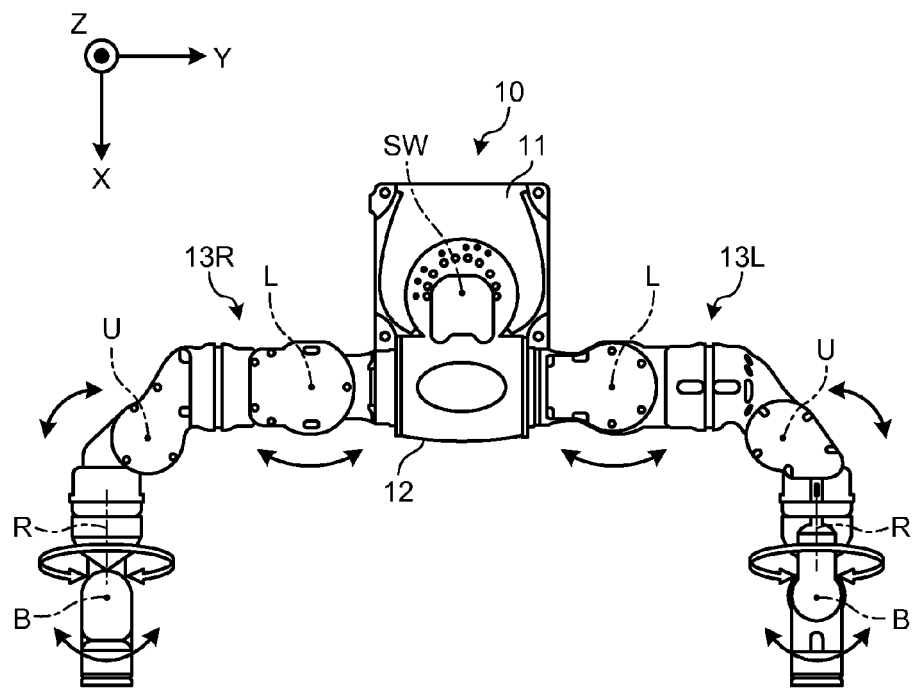
FIG. 3B is a schematic plan view illustrating the constitution of the robot.

First, a constitution example of the robot 10 is explained in conjunction with FIG. 3A and FIG. 3B. FIG. 3A is a front face schematic front view illustrating a constitution of the robot 10, and FIG. 3B is a schematic plan view illustrating the constitution of the robot 10.

As illustrated in FIG. 3A, the robot 10 is a dual-arm type multi-axis robot. To be more specific, the robot 10 includes a pedestal 11, a body 12, a right arm 13R, and a left arm 13L. Here, the left arm 13L is one example of a first arm, and the right arm 13R is one example of a second arm.

The pedestal 11 is fixed on the floor or the like in the inside of the safety cabinet 2 (see FIG. 1A), and supports the body 12 at a distal end portion thereof in a swingable manner about an axis SW (see a two-headed arrow about the axis SW in FIG. 3A).

The body 12 is supported by the pedestal 11 at the proximal end portion thereof, and supports the proximal end portion of the right arm 13R at a right shoulder portion thereof in a rotatable manner about an axis S. In the same manner as above, the body 12 supports the proximal-end portion of the left arm 13L at the left shoulder portion thereof in a rotatable manner about an axis S (see a two-headed arrow about the axis S in each case above).

Each of the right arm 13R and the left arm 13L is constituted of a plurality of links and joints, and is set, in each joint from the proximal-end portion thereof to the distal end portion thereof, in a rotatable manner about each of the axis S, an axis E, and an axis T (see two-headed arrows about the axis S, the axis E, and the axis T in FIG. 3A).

As illustrated in FIG. 3B, each of the right arm 13R and the left arm 13L is set in a rotatable manner about each of an axis L, an axis U, an axis R, and an axis B (see two-headed arrows about the axis L, the axis U, the axis R, and the axis B in FIG. 3B). That is, the robot 10 has 7 axes per arm.

The robot 10 performs various multi-axis operations in which the two arms each having seven axes and the rotation operation about the axis SW are combined with each other based on operation instructions from the controller 30.

Here, the right hand 14R is attached to the distal movable end rotatable about the axis T of the right arm 13R, and the left hand 14L is attached to the distal movable end rotatable about the axis T of the left arm 13L.

Subsequently, the constitution examples of the right hand 14R and the left hand 14L are explained in conjunction with FIG. 4A to FIG. 4D. Here, in the present embodiment, the right hand 14R and the left hand 14L are substantially identical in constitution except that the right hand 14R and the left hand 14L are arranged on the right side and the left side of the body 12, respectively. Therefore, the right hand 14R and the left hand 14L may be referred to collectively as a "hand 14." In the same manner as above, the right arm 13R and the left arm 13L may be referred to collectively as an "arm 13."

Figure 4A:
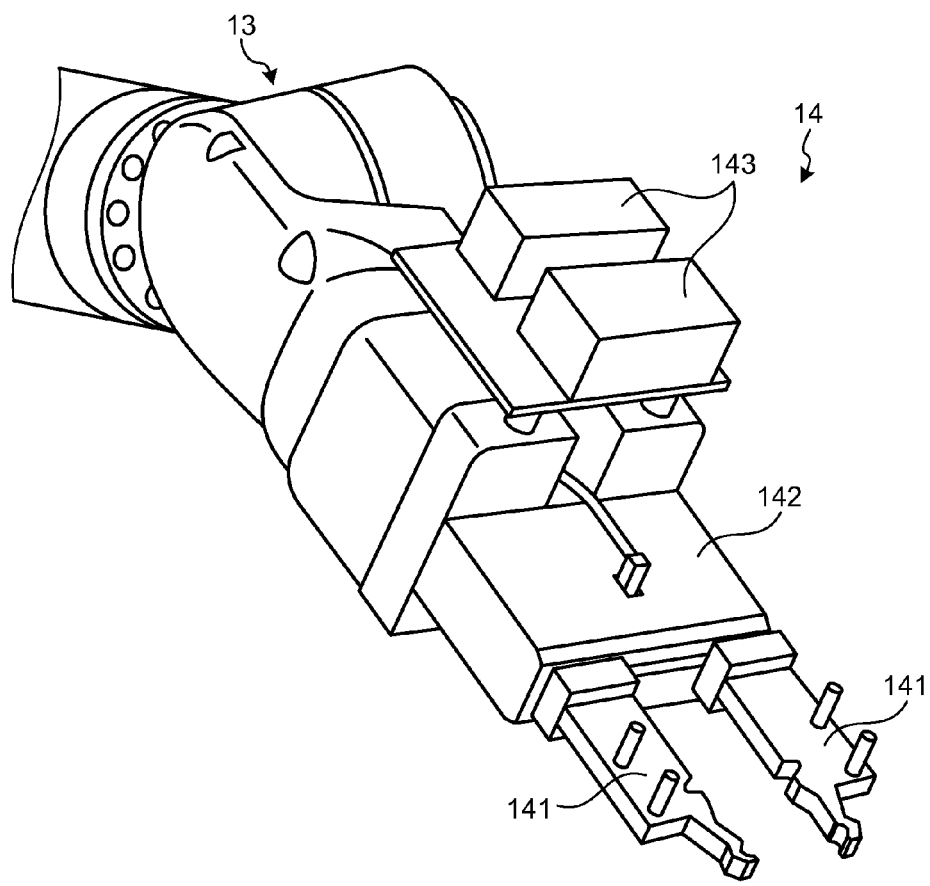
FIG. 4A is a perspective schematic view illustrating a constitution of a hand.
Figure 4B:
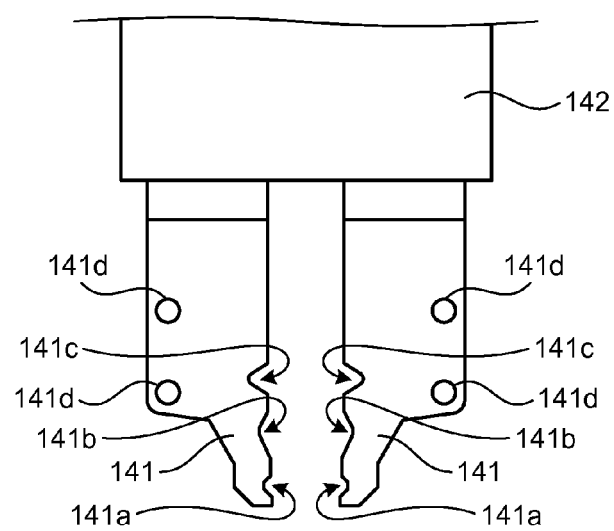
FIG. 4B is a schematic plan view illustrating a constitution of a gripper.
Figure 4C:
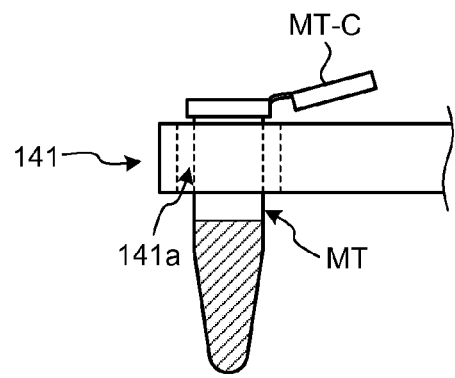
FIG. 4C is a schematic side view illustrating an example of gripping a micro tube.
Figure 4D:
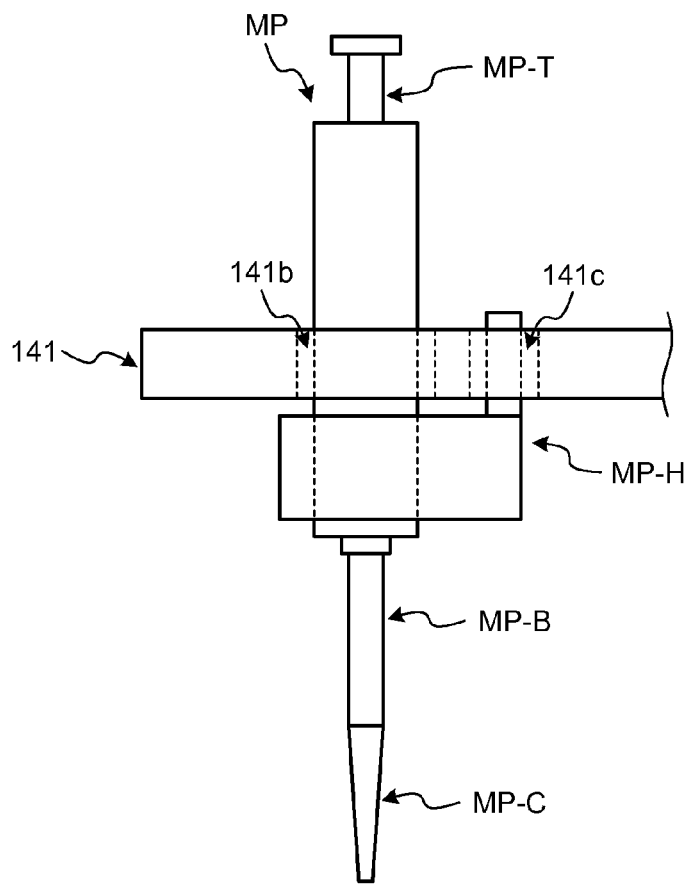
FIG. 4D is a schematic side view illustrating an example of gripping a pipette.

FIG. 4A is a perspective schematic view illustrating a constitution of the hand 14. FIG. 4B is a schematic plan view illustrating a constitution of a gripper 141. FIG. 4C is a schematic side view illustrating an example of gripping the micro tube MT. Furthermore, FIG. 4D is a schematic side view illustrating an example of gripping the pipette MP.

As illustrated in FIG. 4A, the hand 14 includes the gripper 141 (holding mechanism), a base 142, and a camera unit 143. The hand 14 is attached to the distal end portion of the component rotatable of the arm 13 as described above.

The gripper 141 is a pair of parallel opening and closing type gripping jaws arranged in a slidable manner in the direction toward and away from each other. The gripper 141 sandwiches a subject to be gripped between the pair of gripping jaws to grip the subject to be gripped.

The base 142 includes a sliding mechanism that slides the gripping jaws of the gripper 141. The camera unit 143 is an image pick-up device used for identifying a subject to be gripped by picking up an image of the shape or the like of the subject to be gripped.

As illustrated in FIG. 4B, a first recessed portion 141a, a second recessed portion 141b, and a third recessed portion 141c are formed in each of the gripping jaws of the gripper 141. The first recessed portion 141a to the third recessed portion 141c are, for example, formed depending on the respective shapes of subjects to be gripped, the subjects being different in type from each other.

For example, as illustrated in FIG. 4C, the gripper 141 grips the micro tube MT sandwiched between the first recessed portions 141a. Here, the micro tube MT has a cover MT-C, and the gripper 141 is also capable of opening and closing the cover MT-C by using the distal end portion thereof, a jig, or the like. In the explanation made hereinafter, for the sake of convenience, the illustration of the cover MT-C is omitted.

For example, as illustrated in FIG. 4D, the gripper 141 grips the pipette MP sandwiched between the second recessed portions 141b and between the third recessed portions 141c. To be more specific, the pipette MP is held by the above-mentioned pipette stand 27 (see FIG. 1A) in a state that a holder MP-H is attached to the pipette MP, and the gripper 141 grips a handle portion of the holder MP-H sandwiched between the third recessed portions 141c thus holding the pipette MP between the second recessed portions 141b.

Figure 5A:
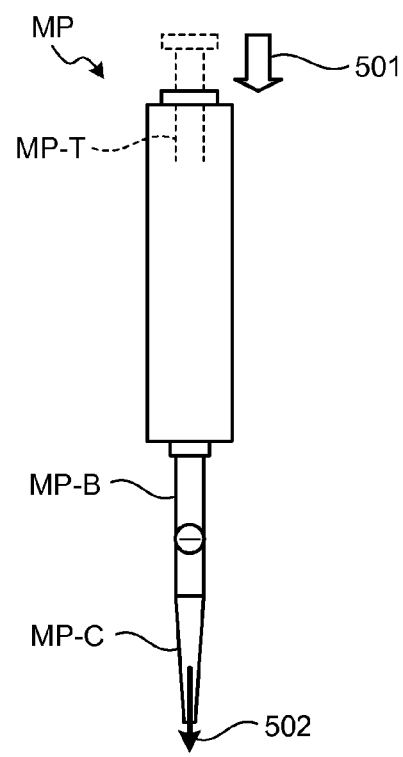
FIG. 5A and FIG. 5B are schematic views (part1) and (part2) each illustrating a constitution of the pipette.
Figure 5B:
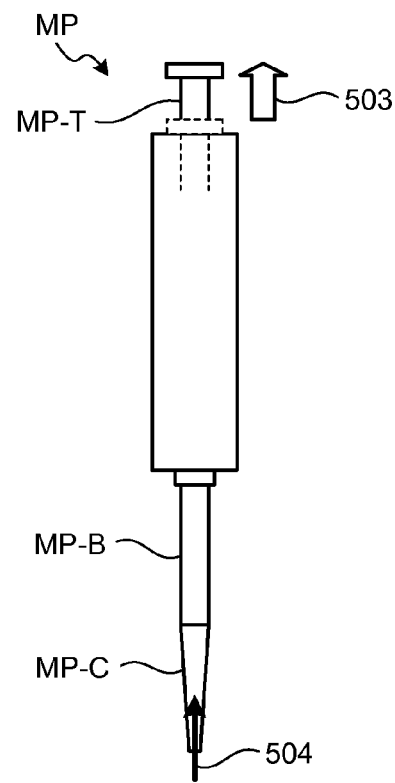

Here, as illustrated in FIG. 4D, the pipette MP has a tip MP-C (suction opening), a body MP-B, and the tail part MP-T. Here, in preparation for the explanation made later, the constitution of the pipette MP is explained in advance. FIG. 5A and FIG. 5B are schematic views (part1) and (part2) each illustrating a constitution of the pipette MP.

As is generally well-known, the pipette MP is a process apparatus for performing suction or pouring of a reagent, a supernatant liquid, or the like. As illustrated in FIG. 5A, the tail part MP-T is depressed and hence, air is discharged from the tip MP-C (see arrows 501 and 502 in FIG. 5A), and negative pressure for sucking a liquid into the body MP-B is generated. Here, a white bordered circle containing "−" (minus) in FIG. 5A indicates that the negative pressure is generated in the inside of the body MP-B.

In this manner, a pressure difference between the inside and outside of the body MP-B is generated and hence, as illustrated in FIG. 5B, the pipette MP sucks, when the depression of the tail part MP-T is released, liquid from the tip MP-C into the body MP-B (see arrows 503 and 504 in FIG. 5B). Furthermore, the body MP-B holds the sucked liquid.

Furthermore, the tail part MP-T is, for example, arranged in such a manner that the tail part MP-T is not depressed in a free state by using a biasing member such as a spring.

Here, as in the present embodiment, when the pipette MP is used as a process apparatus in the biomedical field, it is preferable that the pipette MP be a micropipette capable of measuring and dispensing accurately the volume of a minute amount of liquid (on the order of 1 µl to 1000 µl, for example). Here, the pipette MP is not limited to the micropipette, and may be a transfer pipette, a measuring pipette, a Komagome pipette, a Pasteur pipette, or the like.

In conjunction with FIG. 4B again, a protruding portion 141d of the gripper 141 is explained. The gripper 141 further includes a plurality of protruding portions 141d (four protruding portions in this case). The protruding portion 141d is a member for holding the schale SC (see FIG. 1A).

To be more specific, the robot 10 places, in holding the schale SC, the schale SC on the gripper 141, closes the gripping jaws, and sandwiches the outer periphery of the schale SC with the protruding portions 141d thus gripping the schale SC.

In this manner, the gripper 141 includes the first recessed portion 141a to the third recessed portion 141c and the protruding portions 141d and hence, even when the gripper 141 has only the pair of gripping jaws, a plurality of types of subjects to be gripped can be gripped. That is, a bench work can be performed efficiently without changing the gripper 141 with respect to a large variety of process apparatuses used for the bench work.

Here, in performing a bench work, a process apparatus made of a fragile material is used in many cases and hence, for preventing unnecessary breakages or the like, it is preferable to form, for example, the first recessed portion 141a to the third recessed portion 141c, and the protruding portion 141d in a chamfered manner.

Next, a method for detecting a liquid interface level in the present embodiment is specifically explained. FIG. 6A to FIG. 6D are explanatory views (part1) to (part4) for explaining respective processes of the method for detecting the liquid interface level. Here, the container into which liquid is poured is the micro tube MT.

In the present embodiment, while the gripper 141 holds the micro tube MT, the arm 13 is operated so that the micro tube MT is overlapped with the sensing region SA of the sensor 21b, and the interface of a liquid is detected thus deriving a liquid interface level. Here, the operation of the arm 13 is based on the instructions of the above-mentioned instructor 31a.

Figure 6A:
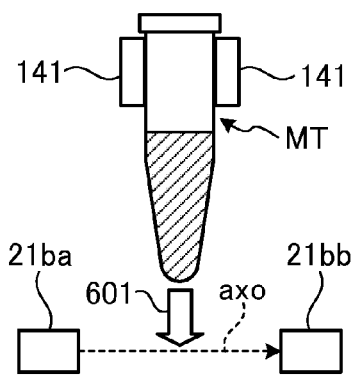
FIG. 6A to FIG. 6D are explanatory views (part1) to (part4) for explaining respective processes of a method for detecting a liquid level.

To be more specific, as illustrated in FIG. 6A, the instructor 31a operates the arm 13 while the gripper 141 holds the micro tube MT, and moves the micro tube MT downwardly so that the micro tube MT enters the sensing region SA in which the optical axis axo is formed by the light emitting part 21ba and the light sensing part 21bb (see an arrow 601 in FIG. 6A).

Figure 6B:
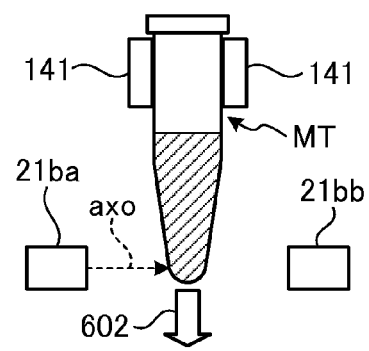

As illustrated in FIG. 6B, the micro tube MT obstructs the optical axis axo, and the sensor 21b detects the liquid in the micro tube MT. In this case, an ON signal is output from the sensor 21b, and obtained by the above-mentioned liquid-interface information obtainer 31b (see FIG. 2). The instructor 31a causes the arm 13 to further move the micro tube MT downwardly (see an arrow 602 in FIG. 6B).

Figure 6C:
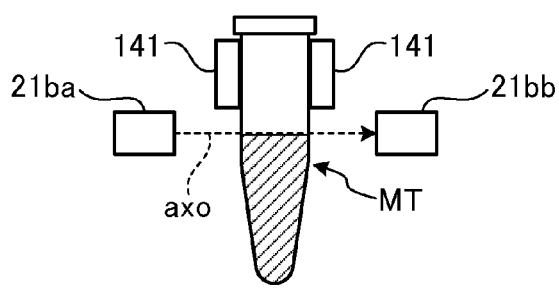

As illustrated in FIG. 6C, the transmission amount of light passing through the sensing region SA in which the optical axis axo is formed changes and hence, the sensor 21b detects the upper surface (that is, the interface) of the liquid in the micro tube MT. In this case, an OFF signal is output from the sensor 21b, and obtained by the liquid-interface information obtainer 31b.

The liquid-interface information obtainer 31b derives a liquid interface level from the positional information of the arm 13 when acquiring the OFF signal.

Figure 6D:
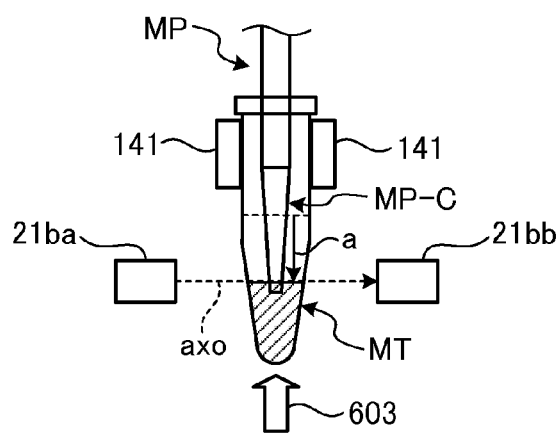

Subsequently, as illustrated in FIG. 6D, the instructor 31a causes the robot 10 to insert the tip MP-C into the micro tube MT and suck liquid with the pipette MP. In this case, even when the liquid interface level in the micro tube MT changes with a suction quantity a, the instructor 31a adjusts the operation of the arm 13 (at least one of the right arm 13R and the left arm 13L) so that the level of the liquid interface is made approximately constant.

To be more specific, the instructor 31a causes the arm 13 to move the micro tube MT upwardly so that the output from the sensor 21b is kept as the OFF signal; for example, along with the lowering of the liquid interface in the micro tube MT (see an arrow 603 in FIG. 6D).

When the ON signal is output from the sensor 21b while the arm 13 moves the micro tube MT upwardly, the speed of moving the micro tube MT upwardly is greater than the speed of lowering the liquid interface and hence, the instructor 31a also performs a speed control so as to suppress the speed of moving the micro tube MT upwardly for keeping the output from the sensor 21b as the OFF signal.

In this manner, in the present embodiment, the operation of the robot 10 is controlled so that the accurate pipetting is performable while the liquid interface level is detected by using the detection unit 21. Accordingly, a bench work can be performed with high accuracy and high reproducibility.

One example of the pipetting operation in the present embodiment is more specifically explained. FIG. 7A to FIG. 7H are schematic views (part1) to (part8) each illustrating one example of the pipetting operation.

Figure 7A:
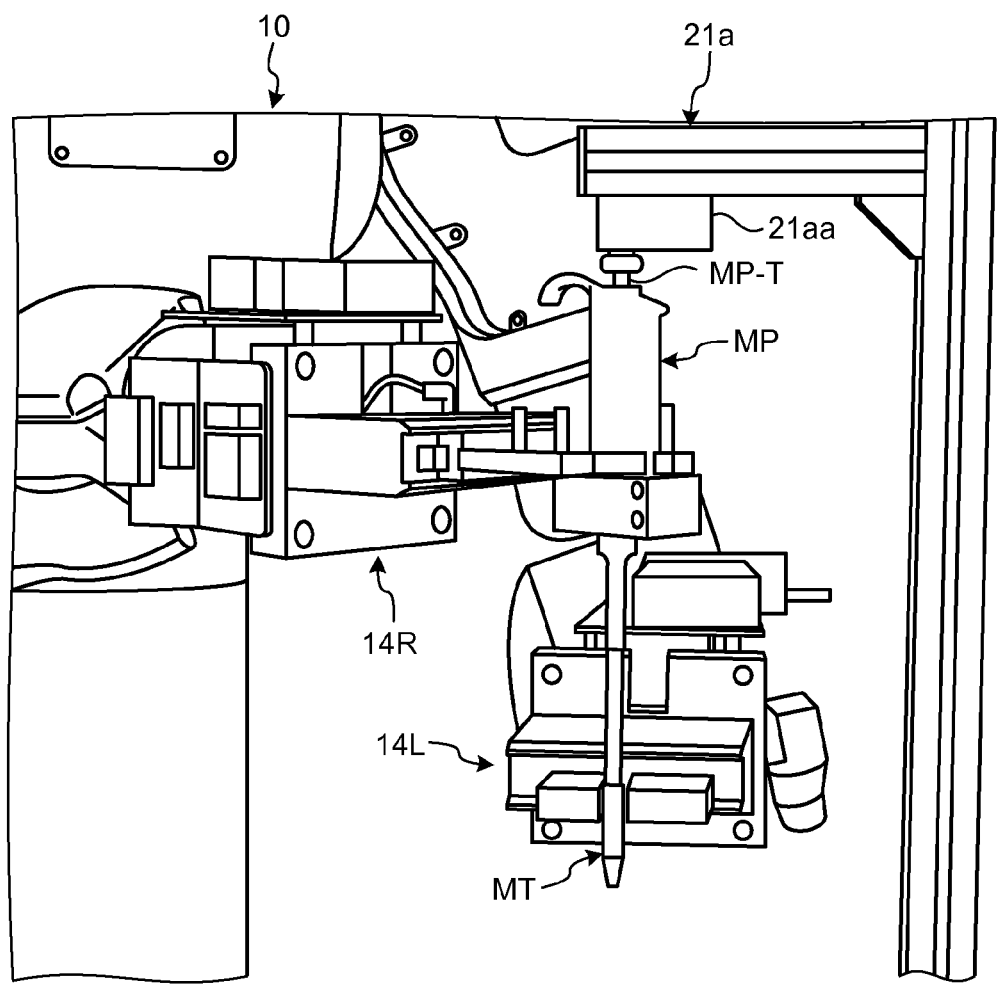
FIG. 7A to FIG. 7H are schematic views (part1) to (part8) each illustrating one example of a pipetting operation.

As illustrated in FIG. 7A, the present embodiment is, for example, configured to cause the robot 10 to perform pipetting while causing the right hand 14R to hold the pipette MP and, at the same time, causing the left hand 14L to hold the micro tube MT.

In this case, the suction of liquid by the pipette MP is performed by the operation such that the robot 10 thrusts the tail part MP-T against the contact part 21aa of the jig 21a, or releases the tail part MP-T thrust.

Figure 7B:
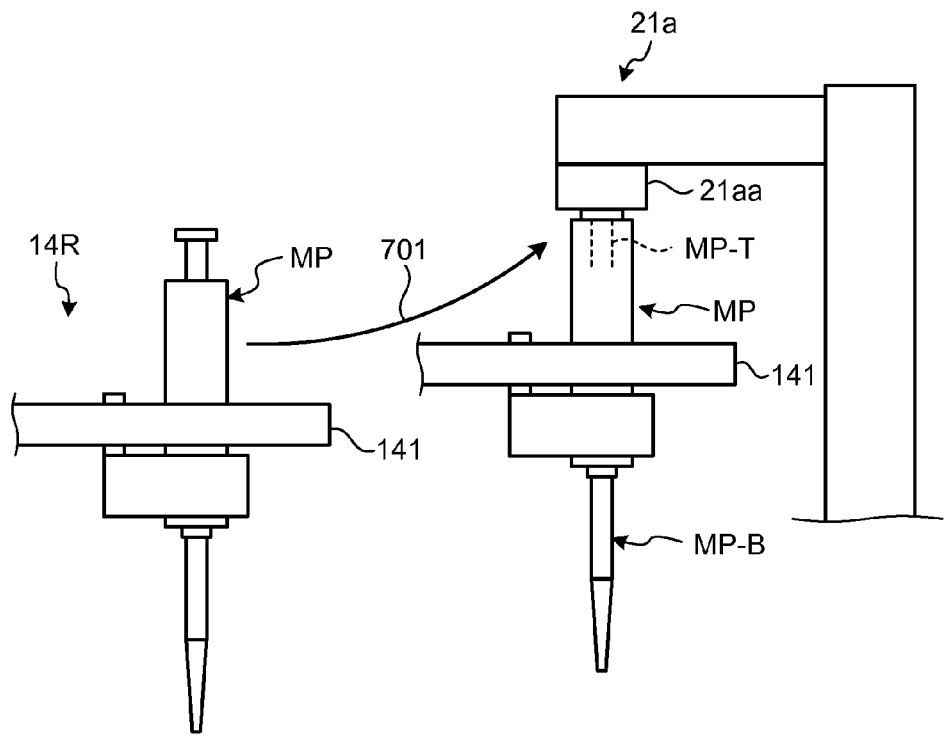

The following provides a more specific explanation. First, as illustrated in FIG. 7B, the instructor 31a causes the robot 10 to hold the pipette MP using the gripper 141 of the right hand 14R, and thrusts the tail part MP-T against the contact part 21aa of the jig 21a (see an arrow 701 in FIG. 7B). Accordingly, the body MP-B is a state in which a negative pressure is generated in the inside of the body MP-B.

Figure 7C:
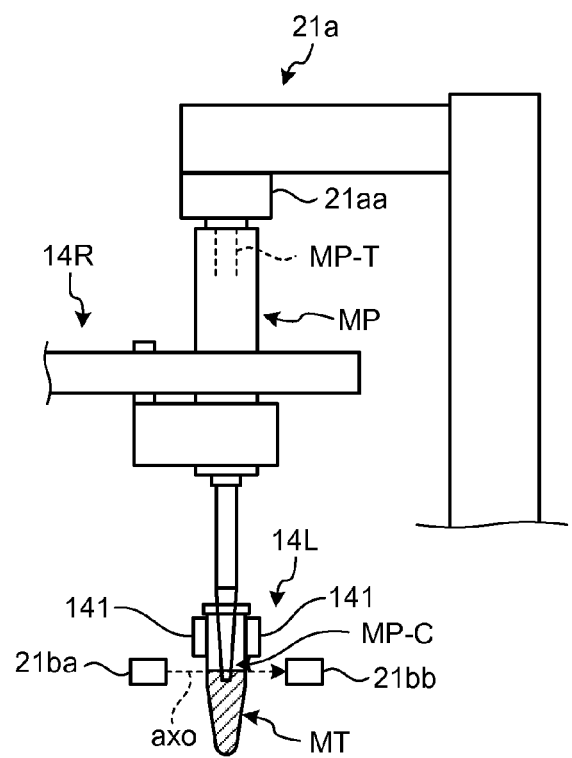

As illustrated in FIG. 7C, the instructor 31a causes the robot 10 to hold the micro tube MT with the use of the gripper 141 of the left hand 14L, and detect a liquid interface level by using the above-mentioned method for detecting the liquid interface level (see FIG. 6A to FIG. 6D). In addition, the instructor 31a causes the robot 10 to insert the pipette MP into the micro tube MT, and place the tip MP-C at a position lower than the liquid interface level.

Figure 7D:
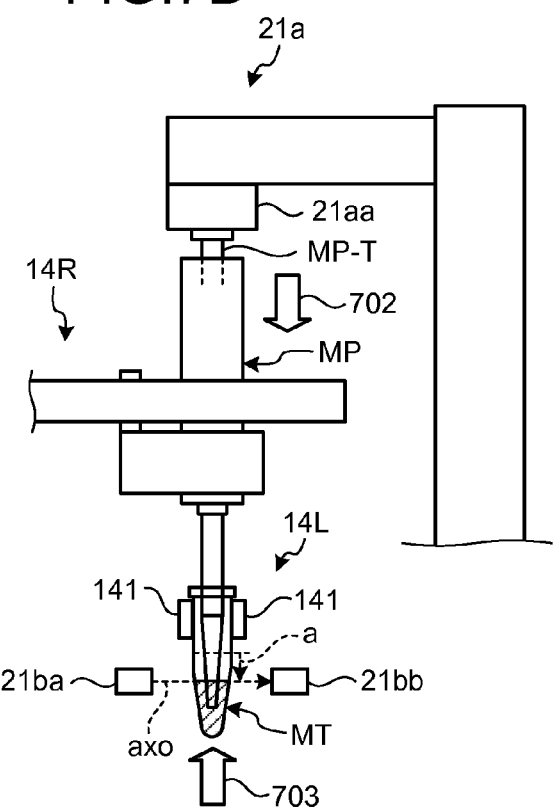

As illustrated in FIG. 7D, the instructor 31a causes the robot 10 to move downwardly the right hand 14R (that is, the right arm 13R) so that a liquid in the micro tube MT is sucked into the pipette MP by releasing gradually the tail part MP-T thrust (see an arrow 702 in a FIG. 7D).

In this case, the instructor 31a causes the robot 10 to move, for example, upwardly the left hand 14L (that is, the left arm 13L) so as to move upwardly the micro tube MT so that the liquid interface level is made approximately constant according to the operation of the right arm 13R (see an arrow 703 in FIG. 7D).

In this manner, in the present embodiment, the instructor 31a operates the right arm 13R so that the pipette MP is inserted into the micro tube MT in a state that the tail part MP-T is thrust against the jig 21a to generate negative pressure in the inside of the body MP-B, the tail part MP-T thrust is released gradually and hence, the liquid is sucked. At the same time, the instructor 31a adjusts the operation of the left arm 13L so that the level of the interface of a liquid is made approximately constant according to the operation of the right arm 13R.

That is, the present embodiment is configured to control the robot 10 in such a manner that a liquid interface level is detected and, at the same time, the right arm 13R and left arm 13L of the robot 10 are operated in cooperation with each other, and the liquid interface level is made approximately constant. Accordingly, the present embodiment realizes a pipetting operation accurately performable thus contributing to performing a bench work with high accuracy and high reproducibility.

Figure 7E:
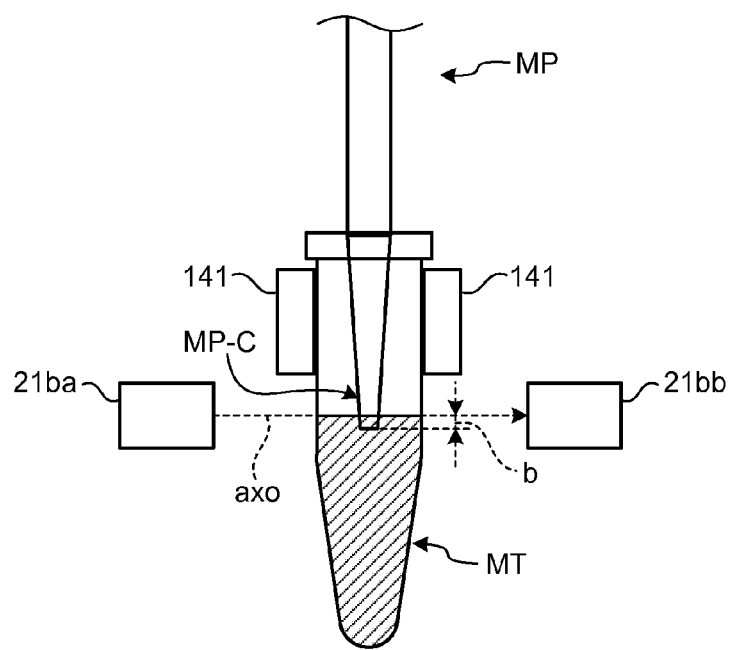

Here, it is preferable that such a cooperation control be performed so that a liquid interface level is made approximately constant and, at the same time, as illustrated in FIG. 7E, the distal end of the tip MP-C of the pipette MP is kept at a position lower than a liquid interface by the predetermined small amount b.

Figure 7F:
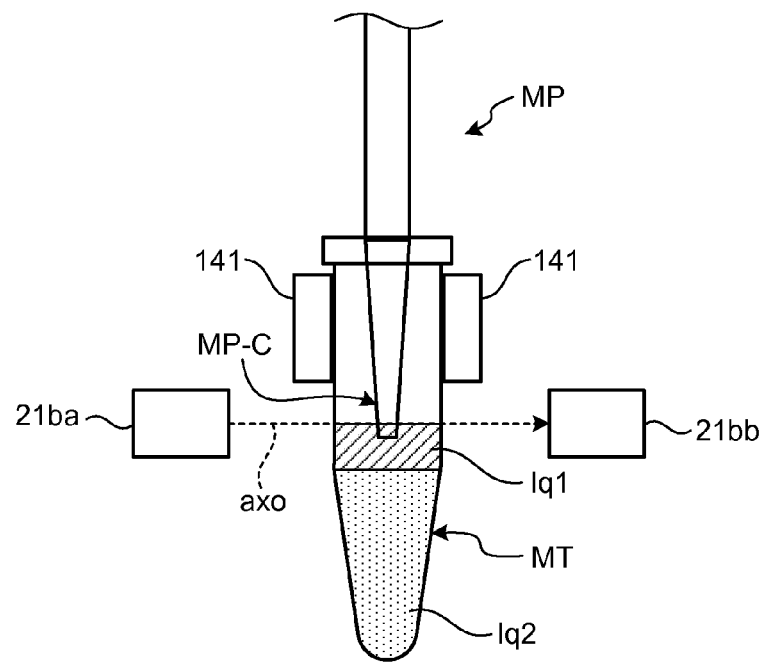

In this manner, the distal end of the tip MP-C is kept at a predetermined position lower than a liquid interface and hence, as illustrated in FIG. 7F, when the liquid is separated into two layers of a supernatant liquid lq1 and a sediment lq2 in the micro tube MT, the pipetting of sucking only the supernatant liquid lq1 can be performed accurately. That is, a bench work can be provided with high accuracy and high reproducibility.

Figure 7G:
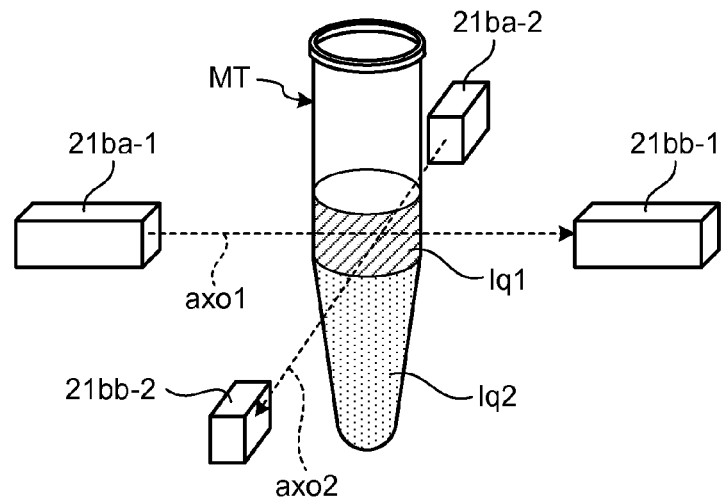

The detection of such a separation interface is achievable by, for example, adopting such a constitution as illustrated in FIG. 7G. That is, a pair of a light emitting part 21ba-1 and a light sensing part 21bb-1 and a pair of a light emitting part 21ba-2 and a light sensing part 21bb-2 are arranged in such a manner that respective optical axes axo1 and axo2 intersect with each other (including a case that the optical axes axo1 and axo2 are arranged in a skew position).

Figure 7H:
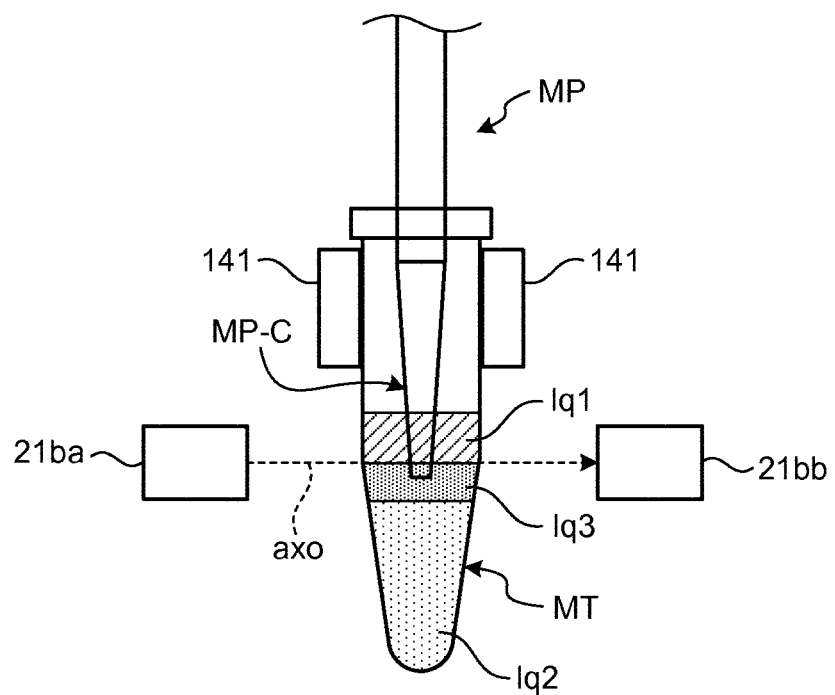

Thresholds of transmission amounts, refractive indexes, or the like of lights detected by the respective pairs of the light emitting parts and the light sensing parts may be set different from each other. Accordingly, for example, as illustrated in FIG. 7H, even when a liquid is separated into three layers of a supernatant liquid lq1, a sediment lq2, and an intermediate layer lq3, the liquid interface level of the intermediate layer lq3 can be detected.

The distal end of the tip MP-C can be kept at a predetermined position lower than the upper surface of the intermediate layer lq3 and hence so as to perform the pipetting of only the intermediate layer lq3. That is, a bench work can be provided with high accuracy and high reproducibility.

Although one example of the pipetting operation using the pipette MP that requires the depression of the tail part MP-T thereof is explained heretofore, the method for detecting a liquid interface level in the present embodiment is also applicable to a case that a vacuum type suction implement AS that requires no depression operation is used.

Figure 8A:
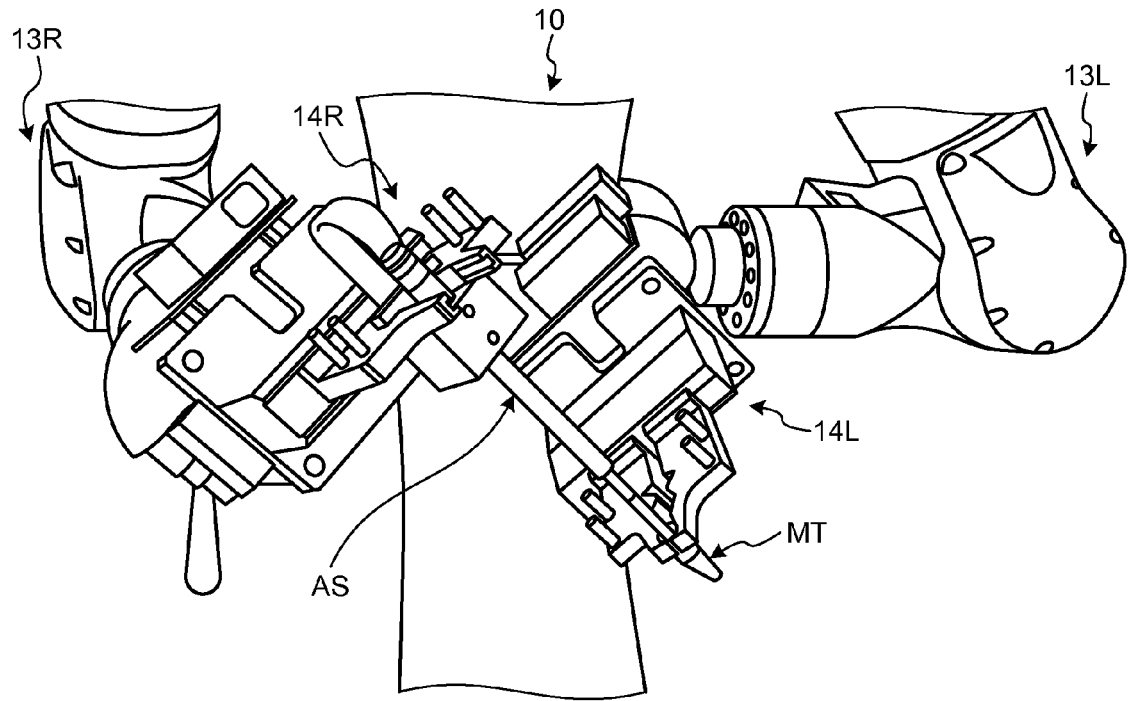
FIG. 8A and FIG. 8B are schematic views (part1) and (part2) each illustrating a modification of the pipetting operation.
Figure 8B:
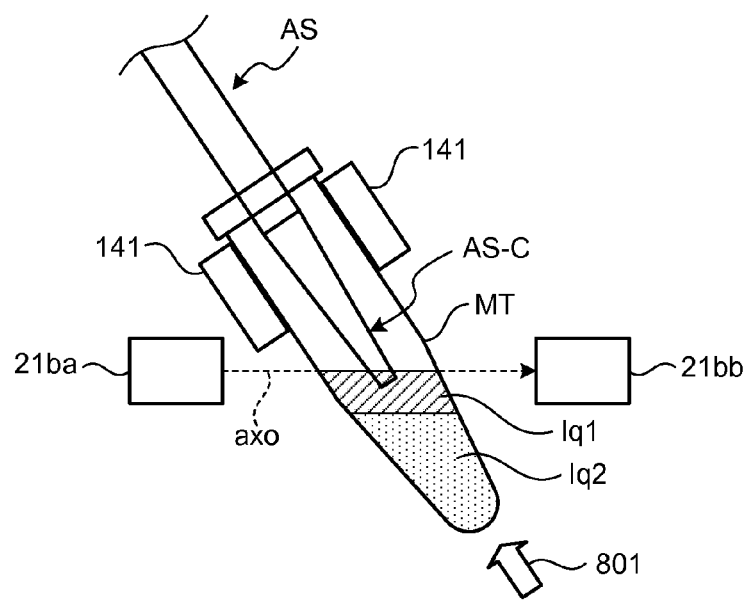

Next, the explanation is made with respect to the above-mentioned case as a modification in conjunction with FIG. 8A and FIG. 8B. FIG. 8A and FIG. 8B are schematic views (part1) and (part2) each illustrating a modification of the pipetting operation.

As illustrated in FIG. 8A, in performing the pipetting, there may be a case that the vacuum type suction implement AS that requires no depression operation is used. For example, FIG. 8A illustrates a case that the right hand 14R holds the vacuum type suction implement AS, and the left hand 14L holds the micro tube MT.

In the vacuum type suction implement AS, since suction through a suction source (not illustrated in the drawings) is performed and hence, it is unnecessary to thrust the above-mentioned tail part MP-T against the jig 21a. Accordingly, as illustrated in FIG. 8A, the liquid can be sucked by the vacuum type suction implement AS arranged in an inclined posture without setting the posture of the vacuum type suction implement AS along a vertical direction.

In this case, as illustrated in FIG. 8B, the liquid interface level can be detected by the sensor 21b (that is, the light emitting part 21ba and the light sensing part 21bb) in such a manner that the micro tube MT is inclined and, at the same time, moved upwardly along the direction in which the vacuum type suction implement AS extends (see an arrow 801 in FIG. 8B).

In this case also, it is preferable that the right arm 13R and the left arm 13L be controlled in cooperation with each other so that the tip AS-C of the vacuum type suction implement AS is kept at a predetermined position lower than the liquid interface in an approximately constant manner.

Accordingly, as illustrated in FIG. 8B, for example, even when a liquid in the inclined micro tube MT is separated into two layers of the supernatant liquid lq1 and the sediment lq2 as mentioned above, the operation of pipetting only the supernatant liquid lq1 can be performed. That is, a bench work can be performed with high accuracy and high reproducibility.

As mentioned above, the robot system according to the embodiment includes a sensor, an arm, and an instructor. The sensor is configured to detect an interface of a liquid. The arm includes a holding mechanism that holds a container containing the liquid. The instructor instructs the arm to cause the container to enter a sensing region of the sensor while holding the container, so as to cause the sensor to detect the interface.

The robot system in the embodiment can perform a bench work with high accuracy and high reproducibility.

Here, in the embodiment mentioned above, although a case that a container containing a liquid is a micro tube is taken as a main example, any type of the container is applicable. For example, a schale or a beaker may be used as the container. It is needless to say that a test tube other than a micro tube may be used.

In the embodiment mentioned above, although the pipetting is mainly taken as a representative example of a bench work, the above-mentioned method of detection is applicable to any bench work provided that the bench work can be performed with high accuracy while detecting the interface of a liquid.

For example, when no liquid is sucked from a container, but dispensed accurately to a container, a robot may adjust the operation of any one of arms thereof so that a liquid interface level of the dispensed liquid is detected so as to keep the liquid interface level approximately constant, and the distal end of a pipette does not excessively enter the liquid whose interface rises.

The embodiment mentioned above is also applicable to a method for inspection. Specifically, the method for inspection may include instructing an arm including a holding mechanism that holds a container containing a liquid to cause the container to enter a sensing region of a sensor while holding the container, and detecting the interface of the liquid in the container that enters the sensing region.

The embodiment mentioned above is also applicable to a method for producing an inspection object. That is, the method for producing the inspection object may include instructing an arm including the holding mechanism that holds the container containing the liquid to cause the container to enter the sensing region of the sensor while holding the container, and detecting the interface of the liquid in the container that enters the sensing region. The method for producing the inspection object is, for example, capable of producing a specimen with respect to a specimen treatment in the biomedical field.

Furthermore, in the embodiment mentioned above, although a case that the robot is a dual-arm robot is taken as an example, the embodiment is not limited to this example. For example, a plurality of single-arm robots may be used.

In addition, in the above-mentioned embodiment, although a robot having seven axes for each arm thereof is exemplified, the number of axes is not limited.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A robot system comprising:
    a sensor configured to detect an interface of a liquid;
    a first arm including a holding mechanism that holds a container containing the liquid; and
    an instructor that instructs the first arm to cause the container to enter a sensing region of the sensor while holding the container, so as to cause the sensor to detect the interface, the instructor instructs the first arm to cause the container to move so that the interface continuously exists in the sensing region in a case where the sensor detects a change in a height position of the interface.

2. The robot system according to claim 1, further comprising:
    a second arm including a holding mechanism that holds a suction implement that sucks the liquid, wherein
    the instructor causes, while adjusting an operation of at least one of the first arm and the second arm so that a level of the interface is made approximately constant based on a detection result of the sensor, the suction implement to suck the liquid from the container.

3. The robot system according to claim 2, wherein
    the suction implement is a pipette that includes a suction opening, a body that holds the liquid sucked, and a tail part that generates a negative pressure for sucking the liquid into the body by being depressed, and
    the container is a micro tube.

4. The robot system according to claim 3, further comprising:
    a jig arranged against which the tail part is capable of being thrust, wherein
    the instructor operates the second arm so that the pipette is inserted into the micro tube in a state that the tail part is thrust against the jig to generate the negative pressure and the tail part thrust is gradually released so that the liquid is sucked and adjusts the operation of the first arm so that the level of the interface is made approximately constant according to the operation of the second arm.

5. The robot system according to claim 1, wherein the interface to be detected by the sensor includes a separation interface formed in the liquid separated into two or more layers.

6. The robot system according to claim 2, wherein the interface to be detected by the sensor includes a separation interface formed in the liquid separated into two or more layers.

7. The robot system according to claim 3, wherein the interface to be detected by the sensor includes a separation interface formed in the liquid separated into two or more layers.

8. The robot system according to claim 4, wherein the interface to be detected by the sensor includes a separation interface formed in the liquid separated into two or more layers.

9. A method for inspection, comprising:
    instructing a first arm including a holding mechanism that holds a container containing a liquid to cause the container to enter a sensing region of a sensor while holding the container;
    detecting an interface of the liquid in the container that has entered the sensing region; and
    instructing the first arm to cause the container to move so that the interface continuously exists in the sensing region in a case where the sensor detects a change in a height position of the interface.

10. A method for producing an inspection object, the method comprising:
    instructing a first arm including a holding mechanism that holds a container containing a liquid to cause the container to enter a sensing region of a sensor while holding the container;
    detecting an interface of the liquid in the container that has entered the sensing region; and
    instructing the first arm to cause the container to move so that the interface continuously exists in the sensing region in a case where the sensor detects a change in a height position of the interface.

11. A robot system comprising:
    a sensor configured to detect an interface of a liquid;
    a first arm including a holding mechanism that holds a container containing the liquid;
    an instructor that instructs the arm to cause the container to enter a sensing region of the sensor while holding the container, so as to cause the sensor to detect the interface; and
    a second arm including a bolding mechanism that holds a suction implement that sucks the liquid, wherein
    the instructor causes, while adjusting an operation of at least one of the first arm and the second arm so that a level of the interface is made approximately constant based on a detection result of the sensor, the suction implement to suck the liquid from the container.

* * * * *